(12) United States Patent
Fukui et al.

(10) Patent No.: US 8,742,128 B2
(45) Date of Patent: Jun. 3, 2014

(54) PROCESS FOR PRODUCING PYRIDINE COMPOUND, AND PYRIDINE COMPOUND

(75) Inventors: Koichi Fukui, Kashima (JP); Takeshi Namekata, Kashima (JP); Ikuo Ito, Kashima (JP)

(73) Assignee: Air Water Inc., Sapporo-shi (JP)

( * ) Notice: Subject to any disclaimer, the term of this patent is extended or adjusted under 35 U.S.C. 154(b) by 0 days.

(21) Appl. No.: 13/265,005

(22) PCT Filed: May 22, 2009

(86) PCT No.: PCT/JP2009/059406
§ 371 (c)(1),
(2), (4) Date: Nov. 4, 2011

(87) PCT Pub. No.: WO2010/134193
PCT Pub. Date: Nov. 25, 2010

(65) Prior Publication Data
US 2012/0041209 A1      Feb. 16, 2012

(51) Int. Cl.
*C07D 211/70* (2006.01)
(52) U.S. Cl.
USPC ........................................................ 546/348
(58) Field of Classification Search
None
See application file for complete search history.

(56) References Cited

U.S. PATENT DOCUMENTS 4,883,881 A * 11/1989 Feitler et al. .................. 546/353

FOREIGN PATENT DOCUMENTS

| JP | 60-215670 A | 10/1985 |
| JP | 61-251662 A | 11/1986 |
| JP | 62-129269 A | 6/1987 |
| JP | 01-261368 A | 10/1989 |
| JP | 02-72161 A | 3/1990 |
| JP | 2001-199960 A | 7/2001 |

OTHER PUBLICATIONS

Joule, J. et al *Heterocyclic Chemistry* NY Wiley 2010, p. 261.*
Katritzky et al., *Comprehensive Heterocyclic Chemistry*, vol. 3, Part 2B, Pergamon Press, 1984, p. 161.
Tanner et al., "On the Structure and Mechanism of Formation of the Lansbury Reagent, Lithium Tetrakis (N-dihydropyridyl)aluminate," *J. Org. Chem*, 1993, 58, pp. 1840-1846.
Hensen et al., "Synthesis and Structural Characterization of (1,4-Dihydropyrid-1-yl)aluminum Complexes," *Inorg.Chem.*, 1999, 38, pp. 4700-4704.
International Search Report mailed on Jul. 14, 2009 for the corresponding International patent application No. PCT/JP2009/059406.
Office Action dated Apr. 16, 2013 issued in corresponding CN patent application No. 200980159412.7 (and English translation).

* cited by examiner

*Primary Examiner* — Heidi Reese
(74) *Attorney, Agent, or Firm* — Posz Law Group, PLC

(57) ABSTRACT

Provided is a process for producing a high-purity pyridine compound from a crude pyridine compound that contains a diazine compound as an impurity, the method including a reaction step of reacting the crude pyridine compound with an aluminum hydride compound, and a distillation step of distilling the product obtained from the reaction step. The aluminum hydride compound preferably contains one or more compounds selected from lithium aluminum hydride and sodium aluminum hydride.

16 Claims, No Drawings

PROCESS FOR PRODUCING PYRIDINE COMPOUND, AND PYRIDINE COMPOUND

CROSS REFERENCE TO RELATED APPLICATIONS

This application is a U.S. national stage application of PCT/JP2009/059406 filed on May 22, 2009.

TECHNICAL FIELD

The present invention relates to a process for producing at least one compound selected from the group consisting of pyridine and derivatives thereof (hereafter, "pyridine compound"), and to a pyridine compound that is obtained by the producing process.

BACKGROUND OF THE INVENTION

Pyridine compounds having a pyridine ring such as pyridine, picoline, and lutidine are widely used as solvents, or as starting materials in various organic synthesis materials, pharmaceuticals and agrochemicals. Various processes for producing pyridine compounds are known. Representative examples of such processes include a process in which pyridine compounds are recovered from tar, as well as synthesis processes typified by the Chichibabin method.

Purification by distillation is an effective purification method of pyridine compounds. However, some impurities cannot be removed by distillation alone, and hence purification methods are the object of ongoing improvement. In particular, various methods have been disclosed as methods for removing coloring substances as well as aging coloration-causing substances.

Examples of such methods include, for instance, the following.

a method wherein distillation is performed after irradiation of a pyridine compound with UV rays (Patent Document 1);

a method wherein a pyridine compound is treated with a halogen such as chlorine, bromine, and iodine (Patent Document 2);

a method involving treatment with activated carbon after formation of a salt by a reaction with an acid (Patent Document 3);

a method that involves performing a treatment with a halogen-containing sulfur or phosphorus compound (Patent Document 4);

a method involving treatment with isocyanates (Patent Document 5);

a method involving that the addition of methanol and water followed by distillation (Patent Document 6);

a method involving contact treatment with a porous resin (Patent Document 7);

a method involving treatment with an oxide or hydroxide of an alkaline earth metal (Patent Document 8);

a method involving treatment with a solid alkali in gas phase (Patent Document 9);

a method involving treatment with a permanganate or bichromate, followed by distillation (Patent Document 10); and a method that involves heating with metallic copper or copper oxide, followed by distillation (Patent Document 11).

The coloring substances and the aging coloration-causing substances which are removed in the above-described methods are not exactly identified. Causative agents are deemed to include amines, alcohols and/or aldehydes.

As described above, numerous methods for removing the coloring substances and the aging coloration-causing substances have been disclosed. However, the produced pyridine compound may contain impurities other than the above-described ones. Examples of such impurities include compounds having a diazine ring in which two carbon atoms of a benzene ring are substituted with nitrogen (diazine compounds) such as compounds having a pyrazine ring (pyrazine compounds), compounds having a pyrimidine ring (pyrimidine compounds) and compounds having a pyridazine ring (pyridazine compounds). No effective removal methods of these substances have been reported.

As in the case of pyridine, impurities comprising such diazine compounds are studied. Pyrazine, pyrimidine and pyridazine are impurities that are particularly likely to be problematic. Table 1 summarizes the normal boiling point and melting point of pyridine, pyrazine, pyrimidine and pyridazine

TABLE 1

| Compound | Normal boiling point (° C.) | Melting point (° C.) |
|---|---|---|
| Pyridine | 115.3 | −42 |
| Pyrazine | 116 | 57 |
| Pyrimidine | 124 | 20 to 22 |
| Pyridazine | 208 | −8 |

As the table shows, pyrazine and pyrimidine, in particular, have a normal boiling point close to that of pyridine, and hence separation of the foregoing cannot be achieved by simple distillation. Espacially, pyrazine and pyridine have very similar normal boiling points, and are thus difficult to separate completely, even by rectification.

Pyrazine has a comparatively strong UV absorption peak in the vicinity of 320 nm (logε in cyclohexane (328nm)=3.02, Non-patent Document 1). By contrast, pyridine lacks such a peak. If pyridine contains pyrazine as an impurity, therefore, the pyrazine exerts a significant influence on the UV absorption of pyridine. In a case where pyridine is used as a reaction starting material or a solvent, the pyrazine present as an impurity may exert likewise a significant influence.

Therefore, a demand exists for a simple and inexpensive method that allows efficiently removing diazines, in particular pyrazine and pyrimidine, from pyridine.

The above considerations apply also to other pyridine compounds. As further examples, Table 2 sets forth a comparison between the normal boiling points of methyl pyridine (picoline), methyl pyrazine, and methyl pyrimidine.

TABLE 2

| Compound | Normal boiling point (° C.) |
|---|---|
| 2-methyl pyridine | 128 to 129 |
| 3-methyl pyridine | 144 |
| 4-methyl pyridine | 145 |
| 2-methyl pyrazine | 135 |
| 4-methyl pyrimidine | 141 to 142 |

There are combinations of compounds of which the normal boiling points are close, although the normal boiling points of the combinations of the compounds are not as close as the normal boiling points of the combination of pyridine and pyrazine. Also, there is a case in which methyl pyrazine, methyl pyrimidine and so forth are contained, as impurities, in pyridine, or a case in which pyrazine, pyrimidine and so forth are contained, as impurities, in methyl pyridine. In such cases as well, separation by distillation is difficult on account of the closeness of the normal boiling points of the compounds.

As described above, the normal boiling points of pyrazine compounds and pyrimidine compounds are often close to that of pyridine compounds, and hence separation relying on distillation alone is difficult. Methods can thus be conceived that exploit differences in chemical properties, as purification methods other than distillation.

The chemical properties of pyridine compounds and diazine compounds are well researched. Pyridine and pyrazine exhibit the following features.

Both pyridine and pyrazine undergo nucleophilic substitution reactions, on carbon atoms, with $NaNH_2$ or the like, to yield amino pyridine and amino pyrazine, respectively.

With alkyl halides, pyridine and pyrazine undergo electrophilic reactions on nitrogen atoms, to yield N-alkyl pyridinium and N-alkyl pyrazinium, respectively.

Both pyridine and pyrazine are oxidized by hydrogen peroxide or the like to yield a corresponding N-oxide. As regards reduction, pyridine and pyrazine yield piperidine and piperazine, respectively, when fully reduced.

It has been reported that pyridine reacts with lithium aluminum hydride to yield dihydropyridyl complexes of aluminum (Non-patent Documents 2 and 3).

Patent Document 1: Japanese Examined Patent Publication No. S43-15977
Patent Document 2: Japanese Examined Patent Publication No. S43-20187
Patent Document 3: Japanese Examined Patent Publication No. S43-21545
Patent Document 4: Japanese Examined Patent Publication No. S46-11502
Patent Document 5: Japanese Examined Patent Publication No. S52-951
Patent Document 6: Japanese Examined Patent Publication No. S54-34736
Patent Document 7: Japanese Examined Patent Publication No. S60-19294
Patent Document 8: Japanese Patent Application Publication No. S60-215670
Patent Document 9: Japanese Examined Patent Publication No. H6-746
Patent Document 10: Japanese Examined Patent Publication No. H6-45597
Patent Document 11: Japanese Patent Application Publication No. 2001-199960
Non-patent Documents
Non-patent Document 1: Comprehensive Heterocyclic Chemistry, Vol. 3, Part 2B, Pergamon Press, 1984
Non-patent Document 2: Dennis D. Tanner and Chi-Ming Yang, J. Org. Chem. 1993, 58, 1840-1846
Non-patent Document 3: Karl Hensen et al., Inorg. Chem. 1999, 38, 4700-4704

DISCLOSURE OF THE INVENTION

As described above, a demand exists for a simple and inexpensive method that allows effectively removing diazine compounds, in particular pyrazine compounds and pyrimidine compounds, from pyridine compounds.

The chemical properties of pyridine compounds and diazine compounds have been the object of various studies, but there are as yet not known simple purification methods that, on the basis of such chemical properties, allow removing diazine compounds contained in pyridine compound.

In the light of the above, it is an object of the present invention to provide a process for producing, efficiently and in a simple manner, a pyridine compound out of a crude pyridine compound containing a diazine compound as an impurity, and to provide a pyridine compound that is produced in accordance with that process.

The inventors tried purification methods of pyridine compounds, as reported thus far, on pyridine containing diazine compounds such as pyrazine and pyrimidine as impurities. In all instances, however, purification was either ineffective or extremely limited.

As a result of diligent research, the inventors found that performing treatment with lithium aluminum hydride on pyridine that containing impurities in the form of diazine compounds such as pyrazine and pyrimidin allows efficiently removing these impurities. The inventors developed the above finding and perfected the present invention as a result.

A process for producing a pyridine compound according to one aspect of the present invention comprises a reaction step of allowing a crude pyridine compound to react with an aluminum hydride compound, and a distillation step of distilling the product obtained from the reacting step.

Herein, the "pyridine compound" denotes a compound having a pyridine ring, namely, at least one compound selected from the group consisting of pyridine derivatives and pyridine. The pyridine compound can be obtained by performing a purification process on a crude product thereof (this crude product is referred to in the present invention as "crude pyridine compound").

A pyridine compound according to one aspect of the present invention comprises pyridine of at least 99.9% by weight, wherein the content of a pyrazine compound is at most 3 ppm by weight and the content of a pyrimidine compound is at most 2 ppm by weight. The pyrazine and pyrimidine content can be quantified, for instance, by gas chromatography.

Pyridine according to another aspect of the present invention comprises pyridine of at least 99.9% by weight, and the absorbance per length at 320 nm is at most 0.04 $cm^{-1}$.

The producing process of the present invention allows producing a high-purity pyridine compound efficiently and in a simple manner.

The producing process allows obtaining a pyridine compound having particularly high pyridine purity, with an extremely reduced content of diazine compounds as impurities. It is often difficult to separate, in particular, pyridine compounds from pyrazine compounds and pyrimidine compounds on account of the closeness of the normal boiling points as shown in Tables 1 and 2. Pyrazine compounds have a comparatively strong UV absorption peak in the vicinity of 320 nm, and thus UV absorption characteristics can be significantly affected if such impurities are present. The invention allows obtaining a pyridine compound having particularly high pyridine purity, such that UV absorption arising from such impurities is extremely low.

Such a pyridine compound has substantially no UV absorption arising from impurities, and can be therefore used, without any problems, in optical applications. Also, it is expected that the pyridine compound can be optimally used as a reaction starting material and as a solvent, and that formation of coloring substances and aging coloration-causing substances can be suppressed in the pyridine compound.

BEST MODE FOR CARRYING OUT THE INVENTION

A detailed explanation follows next on a process for producing a pyridine compound, and a pyridine compound, according to one embodiment of the present invention.

The process for producing the pyridine compound according to one embodiment of the present invention comprises a reaction step of allowing a crude pyridine compound to react with an aluminum hydride compound, and a distillation step of distilling the product obtained from the reacting step.

The pyridine compound of the present invention denotes "a compound having a pyridine ring, namely, at least one compound selected from the group consisting of pyridine derivatives and pyridine". Hereafter, pyridine compounds other than pyridine are also referred to as "substituted pyridines".

The substituents of substituted pyridines are not particularly limited. The number of substituents is likewise not limited, and in case of a plurality of substituents, these may be dissimilar from each other. The substitution position is not particularly limited, so long as it is other than position 1 (N). In terms of enhancing yield and efficiently reducing the impurity content, preferably, the substituents do not react with aluminum hydride compounds.

Particularly preferred examples of the substituents include, for instance, alkyl groups. More preferably, the substituent is an alkyl group having 6 or fewer carbon atoms. Specific examples of alkyl pyridines include, for instance, 2,3, and 4-methylpyridine (α,β and γ-picoline); 2,3, and 4-ethyl pyridine; 2,3, and 4-n-propyl pyridine; 2,3, and 4-isopropyl pyridine; 2,3, and 4-n-butyl pyridine; 2,3, and 4-isobutyl pyridine; 2,3, and 4-secondary-butyl pyridine; 2,3, and 4-tertially-butyl pyridine; 2,3-, 2,4-, 2,5-, 2,6-, 3,4- and 3,5-dimethylpyridine (2,3-, 2,4-, 2,5-, 2,6-, 3,4- and 3,5-lutidine), and 2,3,4-, 2,3,5-, 2,3,6-, 2,4,5-, 2,4,6- and 3,4,5-trimethyl pyridine (2,3,4-, 2,3,5-, 2,3,6-, 2,4,5-, 2,4,6- and 3,4,5-collidine).

In the present invention, the term "diazine compound" denotes a compound having a diazine ring, as the collective denomination of a pyrazine compound (compound having a pyrazine ring), a pyrimidine compound (compound having a pyrimidine ring), and a pyridazine compound (compound having a pyridazine ring).

The preparation method of the crude pyridine compound as the reacting substance of the reaction step is not particularly limited, and the substance may be a synthesized compound according to a method such as the Chichibabin method, or may be a crude product recovered from tar or the like.

In the reaction step, the aluminum hydride compound that reacts with the crude pyridine compound is a compound that has, in the molecule, one or more aluminum-hydride hydrogen bonds (Al—H bonds). Preferably, the aluminum hydride compound is a compound represented by any one of Formulas (1) to (3) below.

$$A[AlH_{4-p}(OR^1)_p] \quad (1)$$

(In Formula (1) A is an alkali metal, p is any from among 0, 1, 2 and 3, and $R^1$ is an alkyl group or an alkoxyalkyl group having an ether group therein);

$$AlHR^2R^3 \quad (2)$$

(wherein $R^2$ and $R^3$ are each independently hydrogen or an alkyl group);

$$AlHR^2R^3(NR^4R^5R^6)_n \quad (3)$$

(wherein $R^2$ and $R^3$ are each independently hydrogen or an alkyl group; n is 1 or 2; $R^4$, $R^5$ and $R^6$ are each independently hydrogen, an alkyl group or an alkenlyl group group; and two or all from among $R^4$, $R^5$ and $R^6$ may be bonded to each other).

Particularly preferred examples of the aluminum hydride compound represented by Formula (1) include lithium aluminum hydride $LiAlH_4$, sodium aluminum hydride $NaAlH_4$ and sodium bis(2-methoxyethoxy)aluminum hydride $NaAlH_2(OCH_2CH_2OCH_3)$.

Particularly preferred examples of the aluminum hydride compound represented by Formula (2) include, for instance, alane $AlH_3$, methyl alane $CH_3AlH_2$, dimethyl alane $(CH_3)_2AlH$, and diisobutyl aluminum hydride $[(CH_3)_2CHCH_2]_2AlH$.

Particularly preferred examples of the aluminum hydride compound represented by Formula (3) include, for instance, trimethylamine alane $AlH_3(N(CH_3)_3)$, triethylamine alane $AlH_3(N(CH_2CH_3)_3)$, diethylmethylamine alane $AlH_3(N(CH_2CH_3)_2(CH_3))$ ethyldimethylamine alane $AlH_3(N(CH_2CH_3)(CH_3)_2)$, N-methylpyrrolidine alane, N-methylmorpholine alane and 1-methyl-3-pyrroline alane.

The above aluminum hydride compounds may be used singly or may be used in the form of mixtures of two or more aluminum hydride compounds. The aluminum hydride compound may be used in the form of a pure substance, or may be used in the form of a solution resulting from dissolving beforehand the aluminum hydride compound in a solvent (for instance, an aliphatic ether such as diethyl ether, a cyclic ether such as tetrahydrofuran, an aliphatic hydrocarbon such as hexane and heptane, or an a aromatic hydrocarbon such as benzene and toluene).

The reaction conditions between the crude pyridine compound and the aluminum hydride compound are not particularly limited, and may be appropriately selected from among various conditions. The reaction temperature can likewise be appropriately selected. The reaction pressure is not particularly limited, and may be atmospheric pressure. Alternatively, the reaction may be carried out under pressurized or reduced-pressure conditions, as the case may require. The reaction time is preferably 1 minute or longer. There is no particular upper limit to the reaction time, provided that the environment is such that no impurity, for instance moisture, intrudes from the exterior.

The mixing ratio between the crude pyridine compound and the aluminum hydride compound is to be decided on the basis of the impurity content, including moisture, in the crude pyridine compound. The moisture content is an issue that deserves particular attention. The aluminum hydride compound must be added so that, after having reacted with all the moisture, there remains a sufficient amount for removing residual impurities. In some cases, the aluminum hydride compound may react with a pyridine compound which has been subjected to dehydration process beforehand.

After the reaction step of comprising a reaction of the crude pyridine compound with an aluminum hydride compound, there is carried out the distillation step of distilling the product obtained from the reacting step. The specific operation of the distillation step is not particularly limited, so long as the pyridine compound can be isolated, by distillation, from the above-described product. For instance, distillation may be performed after removal of an insoluble fraction through filtering of the reaction solution. Alternatively, distillation may be performed directly on the reaction solution, without filtering. More preferably, distillation is performed not just once, but in the form of simple distillation initially, followed by rectification. Distillation may be normal-pressure distillation or reduced-pressure distillation.

The mechanism whereby the diazine compounds, as impurities, are removed from the crude pyridine compound in the present invention is not wholly understood yet, but the usefulness thereof is evident, as shown in the below-described examples.

EXAMPLES

The present invention is explained in more detail below based on examples, but the present invention is not limited in any way to the examples.

(Analysis method)

The analysis method in the present invention was as follows.

(1) Gas chromatography (hereafter, abbreviated to "GC")

Measurements were performed using a GC device by Shimadzu, GC-2014.

The measurement conditions were as follows.

Carrier gas: helium (He), total flow 36.7 mL/min;
Split ratio: 50:1;
Column: DB-WAX (30 m×0.25 mm ID, 0.15 μm film);
Column temperature: temperature (time)=50° C. (min 0 to 10), 50 to 80° C. (min 10 to 20), 80° C. (min 20 to 40);
Detection method: FID;
Vaporizing chamber temperature, detector temperature: 150° C.;
Sample: injection of 2.0 μL using Autoinjector AOC-20i;
Detection limit: concentration corresponding a peak height of twice the noise level in the GC chart.

Under the above measurement conditions, the detection limits for pyrazine and pyrimidine were 2.3 and 1.1 ppm by weight, respectively.

(2) $^1$H NMR analysis

Measurements were performed using a 400 MHz FT-NMR device JNM-ECS400 by JEOL. The solvent was deuterated chloroform and the signal of TMS added thereto at the same time was made a standard of chemical shift.

(3) UV absorption measurement

A sample was placed in a quartz cell having an inner dimension of 1 cm squares, and was measured using a double-beam UV-Vis spectrophotometer UV-1700, by Shimadzu. Immediately before the measurement, pure water was placed on the measurement side and the reference side, to perform zero correction. It was confirmed, in particular, that absorbance was zero at 320 nm in this state. The measurement was carried out thereafter with pure water on the reference side.

(4) Content determination

The content was quantified according to an absolute calibration method on the basis of the surface area of the obtained peaks in the GC measurement that was carried out under the above-described conditions.

(5) Moisture measurement

Moisture was measured using a Karl Fischer-type moisture meter KF-05, by Mitsubishi Chemical Corporation. The titrant and dehydrated solvent used were 1 mg of AQUAMICRON Titrant SS and AQUAMICRON Dehydrated Solvent CP, respectively (both from Mitsubishi Chemical Corporation).

The analysis results for three types of pyridine as starting materials used for purification are as follows.

A) Synthesized pyridine—lot 1
UV:absorbance at 320 nm=0.2640
Impurity content:
Pyrazine 21 ppm by weight, and
Pyrimidine 16 ppm by weight.
$^1$H-NMR(CDCl$_3$):δ=8.60 (m, 2H), 7.63 (m, 1H), and 7.24 (m, 2H).

B) Synthesized pyridine—lot 2
UV: absorbance at 320 nm=0.3027
Impurity content:
Pyrazine 22 ppm by weight, and
Pyrimidine 57 ppm by weight.

$^1$H-NMR(CDCl$_3$):δ=8.60(m, 2H), 7.63(m, 1H), and 7.24 (m, 2H).

C) pyridine reagent: by Wako Pure Chemical Industries
UV: absorbance at 320 nm=0.0524
Impurity content:
Pyrimidine 6 ppm by weight, and
2-methyl pyridine 49 ppm by weight.

The lithium aluminum hydride used for purification was a reagent from Kanto Chemical.

Comparative Example 1

A slurry was obtained by adding 2.0 g of calcium hydride (by Kanto Chemical) to 49.1 g of synthesized pyridine—lot 1. The slurry was stirred for 30 minutes at room temperature, followed by simple distillation at normal pressure. Heating was performed in an oil bath, at a temperature set to 150° C. The top temperature ranged from 112 to 116° C. In the simple distillation there was obtained a 17.2 g (35.0%) fraction. The obtained fraction was subjected to UV measurement. The results showed no improved absorbance at 320 nm.

The analysis results after the treatment were as follows.
UV: 320 nm absorbance=0.2661
Impurity content:
Pyrazine 17 ppm by weight, and
Pyrimidine 12 ppm by weight.
The results are summarized in Table 4.

Example 1

A slurry was obtained by adding 1.53 g of lithium aluminum hydride to 1520.2 g of synthesized pyridine—lot 1. The slurry was stirred for 30 minutes at room temperature, followed by simple distillation under the same conditions as in Comparative example 1, to yield a 1449.7 g fraction. The fraction obtained by simple distillation was subjected to rectification, under the conditions given in Table 3, to yield fractions 1 to 17. The results of GC analysis revealed that the fractions had the same composition. Accordingly, fractions 1 to 17 were mixed into one fraction, as a rectification fraction, to yield 1299 g (85.4%) of purified pyridine. The obtained purified pyridine was subjected to UV measurement. The results showed a significantly decreased absorbance, of 0.0344, at 320 nm. No peaks for pyrazine, pyrimidine or other impurities were observed in the GC analysis of the purified pyridine (Table 4).

TABLE 3

| Fraction No. | Distillate ratio (%) | Bottom temperature (° C.) | Top temperature (° C.) | Pressure (mmHg) | Reflux ratio |
|---|---|---|---|---|---|
| 1 | 0 to 2.1 | 76.2 | 73.2 | 201 | 20 |
| 2 to 5 | up to 27.9 | 73.4 | 73.4 | 201 | 10 |
| 6 | up to 29.5 | 115.2 | 115.2 | Normal pressure | 20 |
| 7 | up to 37.1 | 115.2 | 115.2 | Normal pressure | 10 |
| 8 to 17 | up to 96.5 | 115.4 | 115.4 | Normal pressure | 8 |

Example 2

A slurry was obtained by adding 0.2 g of lithium aluminum hydride to 49.0 g of synthesized pyridine—lot 2. The slurry was stirred for 30 minutes at room temperature. Simple distillation was performed under the same conditions as in Comparative example 1, to yield a 44.2 g (90.2%) fraction of purified pyridine. The obtained purified pyridine was subjected to UV measurement. The results showed a significantly decreased absorbance, of 0.0325, at 320 nm. No peaks for pyrazine, pyrimidine or other impurities were observed in the GC analysis of the purified pyridine (Table 4).

Example 3

A slurry was obtained by adding 1.44 g of lithium aluminum hydride to 991.4 g of synthesized pyridine—lot 1. The slurry was refluxed for 30 minutes, followed by simple distillation under the same conditions as in Comparative example 1. As a result there were obtained an initial fraction of 77.5 g (distillate ratio: 0 to 7.8%), a main fraction of 812.9 g (distillate ratio: up to 89.8%) and a final fraction of 66.0 g (distillate ratio: up to 96.5%). The obtained main fraction (purified pyridine) was subjected to UV measurement. The results showed a significantly decreased absorbance by purified pyridine, of 0.0259, at 320 nm. No peaks for pyrazine, pyrimidine or other impurities were observed (Table 4) in the GC analysis of the main fraction (purified pyridine).

Example 4

A slurry was obtained by adding 0.15 g of lithium aluminum hydride to 100 g of a pyridine reagent. The slurry was refluxed for 30 minutes, followed by simple distillation under the same conditions as in Comparative example 1, to yield an initial fraction of 13.0 g (distillate ratio: 0 to 13.0%), a main fraction of 68.8 g (distillate ratio: up to 81.8%) and a final fraction of 7.8 g (distillate ratio: up to 89.6%). The obtained main fraction (purified pyridine) was subjected to UV measurement. The results showed a significantly decreased absorbance, of 0.0293, at 320 nm. The GC analysis results for the main fraction (purified pyridine) were as follows.
Impurity content:
Pyrazine ND (not observed),
Pyrimidine ND, and
2-methyl pyridine 43 ppm by weight.
The results are summarized in Table 4.

Preparative Example

Preparation of triethylamine alane $AlH_3(NEt_3)$
A slurry was obtained by suspending 7.6 g (200 mmol) of $LiAlH_4$ in 250 mL of hexane, under a nitrogen stream. The slurry was cooled to 15° C. Then, 27.5 g (200 mmol) of triethylamine hydrochloride were added slowly to the slurry with taking care so that the temperature did not rise during the addition. The reaction solution obtained through addition of all the triethylamine hydrochloride to the slurry was then stirred for one hour. Thereafter, the flask holding the reaction solution was transferred into a glove box. The reaction solution was filtered in the glove box. The solvent was distilled off the obtained filtrate, to yield a colorless transparent liquid of triethylamine alane (yield 21.4 g).

Example 5

In a glove box, 0.2 g of the triethylamine alane obtained in the preparative example were added to 20.0 g of synthesized pyridine—lot 1, to yield a solution. The solution after addition of triethylamine alane exhibited an orange color. The solution was left to stand for 30 minutes, and was then filtered using a PTFE filter (0.5 μm), to remove turbidity. The solution having the turbidity removed therefrom was subjected to simple distillation under the same conditions as in Comparative example 1, to yield purified pyridine. The obtained purified pyridine was analyzed by GC. The GC analysis results of the purified pyridine are given in Table 4.
Impurity content: triethylamine 0.07% by weight Example 6

In a glove box, 0.6 g of a 65% toluene solution of sodium bis(2-methoxyethoxy)aluminum hydride (by Kanto Chemical) were added to 20.0 g of the synthesized pyridine—lot 1, to yield a solution. The solution was left to stand for 30 minutes, and was then filtered using a PTFE filter (0.5 μm), to remove turbidity. The solution having the turbidity removed therefrom was subjected to simple distillation under the same conditions as in Comparative example 1, to yield purified pyridine. The obtained purified pyridine was analyzed by GC. The GC analysis results of the purified pyridine were as follows.
Impurity content: toluene 0.08% by weight
The results are summarized in Table 4.

Example 7

Herein, 2-methyl pyrazine (by Tokyo Chemical Industry) was added to a reagent of 2-methyl pyridine (by Kanto Chemical) having a purity of 99.7% by weight, to prepare a 2-methyl pyridine solution containing 2-methyl pyrazine of 27 ppm by weight.
In a glove box, 45 mg of lithium aluminum hydride were added to 30 g of the 2-methyl pyridine solution. The solution after addition was left to stand for 30 minutes, and was then filtered using a PTFE filter (0.5 μm), to remove turbidity. The solution having the turbidity removed therefrom was subjected to simple distillation, to yield purified 2-methyl pyridine. The obtained purified 2-methyl pyridine was subjected to GC analysis. The results revealed that the 2-methyl pyrazine peak had disappeared.

Example 8

Herein, 2-methyl pyrazine (Tokyo Chemical Industry) was added to a reagent of 3-methyl pyridine (Wako Pure Chemical Industries) having a purity of 99.8% by weight, to prepare a 3-methyl pyridine solution containing 16 ppm by weight of 2-methyl pyrazine.
In a glove box, 45 mg of lithium aluminum hydride were added to 30 g of the 3-methyl pyridine solution. The solution after addition was left to stand for 30 minutes, and was then filtered using a PTFE filter (0.5 μm), to remove turbidity. The solution having the turbidity removed therefrom was subjected to simple distillation, to yield purified 3-methyl pyridine. The obtained purified 3-methyl pyridine was subjected to GC analysis. The results revealed that the 2-methyl pyrazine peak had disappeared.

TABLE 4

|  | UV 320 nm absorbance | Pyridine content (% by weight) | Pyrazine content (ppm by weight) | Pyrimidine content (ppm by weight) | Moisture (% by weight) |
| --- | --- | --- | --- | --- | --- |
| Synthesized pyridine - lot 1 | 0.2640 | 99.95 | 21 | 16 | 0.05 |

TABLE 4-continued

|  | UV 320 nm absorbance | Pyridine content (% by weight) | Pyrazine content (ppm by weight) | Pyrimidine content (ppm by weight) | Moisture (% by weight) |
|---|---|---|---|---|---|
| Synthesized pyridine - lot 2 | 0.3027 | 99.94 | 22 | 57 | 0.05 |
| Pyridine reagent | 0.0524 | 99.93 | ND | 6 | 0.06 |
| Comparative example 1 | 0.2661 | 99.95 | 17 | 12 | 0.05 |
| Example 1 | 0.0344 | 99.98 | ND | ND | 0.02 |
| Example 2 | 0.0325 | 99.96 | ND | ND | 0.04 |
| Example 3 | 0.0259 | 99.99 | ND | ND | 0.01 |
| Example 4 | 0.0293 | 99.98 | ND | ND | 0.02 |
| Example 5 | /[1] | 99.92 | ND | ND | 0.01 |
| Example 6 | /[1] | 99.91 | ND | ND | 0.01 |

[1]/not measured

INDUSTRIAL APPLICABILITY

The present invention provides a process for producing a high-purity pyridine compound, containing an extremely small amount of diazine compounds, out of a crude pyridine compound.

The pyridine compound produced according to the process of the present invention can be used as a starting material in organic synthesis compounds, pharmaceuticals and agrochemicals, as a solvent for reactions, and as a solvent for cleaning.

The invention claimed is:

1. A process for producing a pyridine compound from a crude pyridine compound comprising a reaction step of allowing the crude pyridine compound to react with an aluminum hydride compound and a distillation step of distilling the product obtained from the reacting step.

2. The process according to claim 1, wherein impurities contained in the crude pyridine comprise a diazine compound.

3. The process according to claim 2, wherein the diazine compound contains one or more selected from the group consisting of pyrazine compounds and pyrimidine compounds.

4. The process according to claim 1, wherein the pyridine compound comprises one or more compounds selected from the group consisting of pyridine, monoalkyl pyridine, and dialkyl pyridine, and the diazine compound comprises one or more compounds selected from the group consisting of pyrazine, monoalkyl pyrazine, dialkyl pyrazine, pyrimidine, monoalkyl pyrimidine, and dialkyl pyrimidine.

5. The process according to claim 1, wherein the aluminum hydride compound contains one compound having general formula (1) or (2):

wherein A is selected from alkali metals, p is 0, 1, or 2, and $R^1$ is an alkyl group having 1 to 6 carbon atoms or an alkoxyalkyl group having 1 to 6 carbon atoms and an ether group therein;

wherein n is 1 or 2, and $R^2$, $R^3$, and $R^4$, which may be identical or different from each other, are a hydrogen or a substituent group, two or all of $R^2$, $R^3$, and $R^4$ being allowed to be connected together to form one moiety of the compound.

6. The process according to claim 1, wherein the aluminum hydride compound contains one or more compounds selected from lithium aluminum hydride and sodium aluminum hydride.

7. The process according to claim 2, wherein the pyridine compound comprises one or more compounds selected from the group consisting of pyridine, monoalkyl pyridine, and dialkyl pyridine, and the diazine compound comprises one or more compounds selected from the group consisting of pyrazine, monoalkyl pyrazine, dialkyl pyrazine, pyrimidine, monoalkyl pyrimidine, and dialkyl pyrimidine.

8. The process according to claim 3, wherein the pyridine compound comprises one or more compounds selected from the group consisting of pyridine, monoalkyl pyridine, and dialkyl pyridine, and the diazine compound comprises one or more compounds selected from the group consisting of pyrazine, monoalkyl pyrazine, dialkyl pyrazine, pyrimidine, monoalkyl pyrimidine, and dialkyl pyrimidine.

9. The process according to claim 2, wherein the aluminum hydride compound contains one compound having general formula (1) or (2):

wherein A is selected from alkali metals, p is 0, 1, or 2, and $R^1$ is an alkyl group having 1 to 6 carbon atoms or an alkoxyalkyl group having 1 to 6 carbon atoms and an ether group therein;

wherein n is 1 or 2, and $R^2$, $R^3$, and $R^4$ which may be identical or different from each other, are a hydrogen or a substituent group, two or all of $R^2$, $R^3$, and $R^4$ being allowed to he connected together to form one moiety of the compound.

10. The process according to claim 3, wherein the aluminum hydride compound contains one compound haying general formula (1) or (2):

wherein A is selected from alkali metals, p is 0, 1, or 2, and $R^1$ is an alkyl group haying 1 to 6 carbon atoms or an alkoxyalkyl group having 1 to 6 carbon atoms and an ether group therein;

wherein n is 1 or 2, and $R^2$, $R^3$ and $R^4$, which may be identical or different from each other, are a hydrogen or a substituent group, two or all of $R^2$, $R^3$, and $R^4$ being allowed to be connected together to form one moiety of the compound.

11. The process according to claim 2, wherein the aluminum hydride compound contains one or more compounds selected from lithium aluminum hydride and sodium aluminum hydride.

12. The process according to claim 3, wherein the aluminum hydride compound contains one or more compounds selected from lithium aluminum hydride and sodium aluminum hydride.

13. The process according to claim 4, wherein the aluminum hydride compound contains one or more compounds selected from lithium aluminum hydride and sodium aluminum hydride.

14. The process according to claim 5, wherein the aluminum hydride compound contains one or more compounds selected from lithium aluminum hydride and sodium aluminum hydride.

15. A method for producing a pyridine compound from a crude pyridine compound mixture containing an impurity including at least one diazine compound, the method comprising:

obtaining the crude pyridine compound mixture containing the impurity;

reacting the crude pyridine compound with an aluminum hydride compound selected from the group consisting of lithium aluminum hydride, sodium aluminum hydride, a compound having general formula (1), a compound having general formula (2) and mixtures thereof, wherein:

$$A[AlH_{4-p}(OR^1)_p] \qquad (1)$$

wherein A is selected from alkali metals, p is 0, 1, or 2 and $R^1$ is an alkyl group having 1 to 6 carbon atoms or an alkoxyalkyl group having 1 to 6 carbon atoms and an ether group therein;

$$AlH_3(NR^2R^3R^4)_n \qquad (2)$$

wherein n is 1 or 2, and $R^2$, $R^3$, and $R^4$, which may be identical or different from each other, are a hydrogen or a substituent group, two or all of $R^2$ $R^3$, and $R^4$ being allowed to be connected together to form one moiety of the compound; and distilling the product obtained from the reacting step and producing a purified pyridine compound substantially free of the impurity.

16. The method according to claim 15, wherein the pyridine compound comprises one or more compounds selected from the group consisting of pyridine, monoalkyl pyridine and dialkyl pyridine, and the diazine compound comprises one or more compounds selected from the group consisting of pyrazine, monoalkyl pyrazine, dialkyl pyrazine, pyrimidine, monoalkyl pyrimidine and dialkyl pyrimidine.

* * * * *